United States Patent [19]

Curry

[11] 3,959,459

[45] May 25, 1976

[54] INHIBITING PERSPIRATION WITH TETRAKIS-(TRIALKYL SILOXY) COMPOUNDS

[75] Inventor: John D. Curry, Oxford, Ohio

[73] Assignee: The Procter & Gamble Company, Cincinnati, Ohio

[22] Filed: Oct. 4, 1971

[21] Appl. No.: 186,534

[52] U.S. Cl..................................... 424/66; 424/65
[51] Int. Cl.² ...................... A61K 7/32; A61K 7/34
[58] Field of Search.......................... 424/47, 65, 66; 260/429.3, 429.5

[56] References Cited
UNITED STATES PATENTS 3,046,268   7/1962   Cohen...................... 260/429.3

OTHER PUBLICATIONS

Feld et al., The Organic Chemistry of Titanium, (1965), pp. 96–97.

Wells et al., Cosmetics & The Skin 1964, pp. 344–357.

*Primary Examiner*—Stanley J. Friedman
*Attorney, Agent, or Firm*—Charles R. Wilson; Richard C. Witte; Thomas H. O'Flaherty

[57] ABSTRACT

Antiperspirant compositions containing tetrakis-(trialkylsiloxy)-titanate or zirconate compounds as antiperspirant agents.

3 Claims, No Drawings

INHIBITING PERSPIRATION WITH TETRAKIS-(TRIALKYL SILOXY) COMPOUNDS

BACKGROUND OF THE INVENTION

This invention relates to novel compositions for topical application to human skin to inhibit perspiration.

One of the most widely used types of cosmetic compositions are the antiperspirants which are designed to inhibit or reduce unwanted perspiration, especially in the axillae. Such compositions generally contain one or more ingredients which inhibit or arrest perspiration flow when applied to human skin. These antiperspirant ingredients are thought to react with the sweat duct by any of a variety of mechanisms and to stop perspiration flow either by a physiological action, or by a physical plugging of the sweat duct. Heretofore, commercially available antiperspirant ingredients have been limited almost exclusively to the partially hydrated acid salts of polyvalent metals, for example the aluminum chlorhydrates, aluminum chloralcoholate compounds, zirconium halide hydrates and the like.

The antiperspirant compounds currently employed all suffer from various defects which limit their utility in day-to-day cosmetic use. For example, many of the commonly used polyvalent metal salts are not sufficiently soluble in organic solvents, especially ethyl alcohol, to allow the formulation of liquid antiperspirant compositions. This recognized defect has been partially overcome by use of such materials as the aluminum chlorhydrate "alcoholates", but these materials generally exhibit reduced antiperspirant effectiveness. In addition, the acid salts of the polyvalent metals sometimes cause an acid reaction on the skin which deteriorates clothing coming in contact therewith. Certain of the known antiperspirant compounds are not sufficiently stable to insure reasonable product shelf life. At the same time, it is well recognized that some antiperspirant compounds apparently are not effective when applied to certain individuals. For these reasons, there is a continuing search for new, effective antiperspirant compounds capable of being formulated into cosmetically acceptable compositions.

Therefore, it is a primary object of this invention to provide new and effective antiperspirant compositions. It is a further object to provide antiperspirant compositions containing certain solvent-soluble tetrakis-(trialkylsiloxy)titanates or tetrakis-(trialkylsiloxy)-zirconates as the antiperspiration ingredient. These and other objects are obtained by the present invention as will become apparent from the following disclosure.

SUMMARY OF THE INVENTION

The present invention is based on the unexpected utility of tetrakis-(trialkylsiloxy)titanate and tetrakis-(trialkylsiloxy)zirconate compounds as antiperspirants. This invention thus encompasses antiperspirant compositions containing an effective amount of said tetrakis-(trialkylsiloxy)titanate or tetrakis-(trialkylsiloxy)-zirconate compounds of the type hereinafter disclosed as the antiperspiration ingredient. (The term "antiperspirant" as used herein encompasses materials that either inhibit, or stop, perspiration flow when applied to the surface of the human skin.)

DETAILED DESCRIPTION OF THE INVENTION

In one of its embodiments, the instant invention encompasses an antiperspirant composition comprising: (1) an amount sufficient to inhibit perspiration (at least about 1.0% by weight, preferably from about 1% to about 20% by weight) of a tetrakis-(trialkylsiloxy) compound of the general formula $$M(OSiR_3)_4 \quad (I)$$

wherein M is selected from the group consisting of titanium and zirconium and wherein each substituent R is alkyl, cycloalkyl, or branched chain alkyl of from about $C_1$ to about $C_{14}$, preferably $C_1$ to about $C_3$; and (2) a pharmaceutically acceptable carrier. Compounds of formula (I), above, wherein one or more of the substituent groups, R, are aryl (e.g., phenyl, methoxyphenyl, etc.) or substituted alkyl (e.g., chloroalkyl, hydroxyalkyl) can also be used herein. However, some of these compounds are difficult to prepare, expensive, and some have undesirable solubility properties and are, thus, not preferred for use herein. Compounds of formula (I) are generically classified as tetrakis-(trialkylsiloxy)titanium compounds (or "titanates") and tetrakis-(trialkylsiloxy)zirconium compounds (or "zirconates") and are sometimes referred to merely as "siloxy-titanates" and "siloxy-zirconates".

This invention also encompasses a method of inhibiting perspiration comprising applying to the human skin an effective amount of a titanium or zirconium compound of formula (I), above.

The tetrakis-(trialkylsiloxy)titanium and tetrakis-(trialkylsiloxy)zirconium compounds of formula (I) useful herein can be prepared using various methods well-known to those skilled in the art. For example, titanium tetrachloride or zirconium tetrachloride can be reacted with four moles of a trialkyl silanol in the presence of ammonia or an amine according to the reaction scheme:

$$MCl_4 + 4(CH_3)_3SiOH + 4NH_3 \rightarrow M[OSi(CH_3)_3]_4 + 4NH_4Cl$$

wherein M is titanium or zirconium.

Alternatively, the trans-esterification technique of Bradley and Thomas, *Chem. J Ind.*, (1958) 17, can be employed according to the following scheme:

$$4RCO_2SiR_3 + M(OR'')_4 \rightarrow M(OSiR_3)_4 + 4RCO_2R''$$

wherein M is titanium or zirconium and R'' is lower alkyl or acyl.

Still another process suitable herein is that of Andrianov, et. al., *Zh. prikl. Khim.*, 32, (1959) 463, as follows:

$$4[Pb(OSiR_3)_2.0.5\ Pb(OH)_2] + 3MCl_4 \rightarrow 2M(OSiR_3)_4 + 6PbCl_2 + M(OH)_4$$

wherein M and R are as above.

Exemplary tetrakis-(trialkylsiloxy)titanates and tetrakis-(trialkylsiloxy)zirconates of formula (I) suitable for use as antiperspirants include tetra-kis-(trimethylsiloxy)titanate, tetrakis-(trimethylsiloxy)-zirconate, tetrakis-(triethylsiloxy)titanate, tetrakis-(triethylsiloxy)zirconate, tetrakis-(triisopropylsiloxy)-titanate, tetrakis-(tri-tetrabutylsiloxy)titanate, tetrakis-(tri-tetradecylsiloxy)zirconate, tetrakis-(methyldipropylsiloxy)titanate, tetrakis-(methyldiethylsiloxy)zirconate, and the like. Preferred compounds are tetrakis-(triethylsiloxy)titanate and tetrakis-(triethylsiloxy)zirconate. Any of the foregoing compounds can be prepared using the general procedures hereinabove detailed.

To effect the antiperspirant activity of the tetrakis-(trialkylsiloxy)-titanium or tetrakis-(trialkylsiloxy)-zirconium compounds of formula (I) in the manner of this invention, said compounds are applied to the human skin in an amount sufficient to inhibit perspiration. The requisite amount of the titanium or zirconium compound of formula (I) will vary since the antiperspirant response to these materials will vary between individuals applying same. In most cases, perspiration, especially axillary perspiration, will be inhibited when at least about 0.01 mg. of the tetrakis-(trialkylsiloxy)-titanium or tetrakis-(trialkylsiloxy)zirconium compound is applied per $mm^2$ of skin. In some instances less material will be needed. Most generally, from about 0.1 g. to 5 g. of an antiperspirant composition, as hereinafter described, containing from about 1% to about 20% by weight of one or more of the titanium or zirconium compounds of formula (I), above, is applied to a skin area of about 24 $cm^2$ with good antiperspirant results. More or less of such compositions can be used, depending on the individual.

It is not necessary that the siloxy-titanate or siloxy-zirconate compounds of formula (I) be dissolved prior to application to effect their antiperspirant action and, when such materials are applied to human skin in the form of a powder, dust or paste, they exhibit a high degree of antiperspirant activity. When the titanium or zirconium compounds of formula (I) are applied as powders in the manner of this invention, their state of aggregation is of no consequence in that they perform their antiperspirant function regardless of particle size. For most cosmetic applications it is desirable that solid materials applied to the skin be impalpable. Therefore, cosmetically acceptable antiperspirant dusts comprising the herein disclosed titanium or zirconium compounds should preferably have said compounds in a state of aggregation smaller than about 37 microns.

In most instances the siloxy-titanium and siloxyzirconium compounds of formula (I) will be applied to human skin in conjunction with a carrier of the type hereinafter detailed. A variety of compatible and pharmaceutically acceptable carriers are suitable for this purpose. By "compatible" is meant that such carriers do not detrimentally react with or decompose the compounds of formula (I). By "pharmaceutically acceptable" is meant that the carriers are suitable for repeated application to human skin with little, or no, untoward physiological effects.

For example, the tetrakis-(trialkylsiloxy)titanates and tetrakis-(trialkylsiloxy)zirconates of formula (I) can be applied to the skin as solutions containing an effective amount, i.e., greater than about 1% by weight, preferably about 1% to about 20% by weight, of said titanium or zirconium compounds. As is noted hereinabove, the choice of carriers for the siloxytitanates and siloxy-zirconates is not limited other than that they be compatible and pharmaceutically acceptable, as herein defined.

Preferably, the antiperspirant titanates and zirconates of formula (I) are dissolved in a solvent prior to application to the skin. There are a variety of solvents which can be used herein to prepare solutions of the compounds of formula (I) for antiperspirant use. For example, alcohols, especially alcohols having from 1 to about 16 carbon atoms; esters, especially those liquid esters of lower organic acids and alcohols having from about 1 to about 16 carbon atoms; polyoxyalkylene materials, for example polyoxyethylene in the molecular weight range from about 50 to about 10,000, are all suitable for use as solvents in the antiperspirant compositions of this invention. Non-limiting examples of compatible, pharmaceutically acceptable solvents suitable for use in preparing antiperspirant compositions containing one or more of the siloxy-titanates or siloxy-zirconates of formula (I) in solution include: ethyl alcohol, isopropyl alcohol, butanol, isobutanol, 2-ethyl-1-hexanol, hexadecanol, methyl propionate, ethyl formate, decyl formate, methyl decanoate, isopropyl myristate and the like. Oily and waxy materials are also suitable for this purpose. For example: waxes, for instance the high molecular weight esters obtained from various plant and animal sources; oils, for example sunflower oil, turtle oil, mink oil, safflower oil, civet oil, and other oils commonly employed in cosmetic applications; high molecular weight alcoholic materials, for example sterols such as $\beta$-sitosterol and campesterol and materials such as cholesterol; lanolin and the commercially available alkylated and alkanoylated lanolins which are commonly employed in cosmetic formulations; higher molecular weight polyoxyalkylene materials which are semi-solid or waxy solids; and high molecular weight waxy hydrocarbons, e.g., petrolatum, are all suitable for use in the compositions herein. Carboxyalkyl celluloses and high molecular weight polyoxyalkylene materials can be used in the formulations herein as gelling agents. Such materials are suitable herein, singly and in mixtures, both by virtue of their compatibility and their pharmaceutical acceptability. Especially preferred compatible, pharmaceutically acceptable carriers for use herein in the preparation of antiperspirant compositions containing the titanate or zirconate compounds of formula (I) are ethyl alcohol, isopropyl alcohol, polyoxyethylene materials and mixtures thereof.

Alternatively, the titanium and zirconium compounds of formula (I) can be formulated in antiperspirant compositions wherein said compounds are not dissolved in the carrier but are merely suspended therein in particulate form. For example, a composition comprising greater than about 0.5% by weight, preferably from about 1% to about 20% by weight, of a particulate siloxy-titanate or siloxy-zirconate of formula (I) and a compatible, pharmaceutically acceptable solid or liquid carrier in which said titanate or zirconate compound is essentially insoluble provides an effective antiperspirant composition. Some of the siloxy-titanates and zirconates herein are tacky solids or liquids. These can be incorporated into antiperspirant compositions in particulate form by pre-adsorption on a solid carrier such as talc, kieselguhr, fuller's earth and the like.

The hereinabove described oily carrier materials useful herein fall within that class of compounds commonly referred to as skin emollients. As is recognized in the art, such emollient materials are often employed in conjunction with many of the materials hereinabove referred to as solvents for the tetrakis-(trialkylsiloxy)-titanium and tetrakis-(trialkylsiloxy)zirconium antiperspirant compounds. Such combinations of the solvent materials and emollient materials also provide carrier mixtures suitable for use herein in the formulation of antiperspirant compositions containing the titanium or zirconium compounds of formula (I).

Still another class of carriers which are suitably employed with the titanium and zirconium compounds of formula (I) include those halogenated, i.e., chlorinated, fluorinated and chloro-fluorinated, lower molecular weight hydrocarbons which are commercially used as aerosol propellants. Many of these materials have vapor pressures of 1 atmosphere, or greater, at temperatures of about −20°C, and above, but are commonly liquified under pressure and employed as propellants in aerosol cosmetic formulations. These liquified gases can be employed to propel antiperspirant solutions of the siloxy-titanates and siloxy-zirconates by mixing said solution with the liquified propellant gas under pressure. In an alternate mode, the siloxy-titanate or siloxy-zirconate can be dissolved or suspended in the pressurized liquified gas, itself. Commonly, antiperspirant compositions comprising liquified propellant gases and antiperspirant ingredients also contain one or more emollients of the type hereinbefore noted. Such compositions comprising a dissolved or undissolved tetrakis-(trialkylsiloxy)titanate or tetrakis-(trialkylsiloxy)zirconate of formula (I), a liquified propellant gas and one or more of said emollient materials are also within the scope of this invention. Antiperspirant compositions comprising from about 1% to about 10% by weight of dissolved or undissolved siloxy-titanate or siloxy-zirconate of formula (I) in combination with from about 80% to 90% by weight of liquified propellant gas, from about 2% to about 10% by weight of a compatible, pharmaceutically acceptable emollient as hereinabove disclosed and, optionally, from about 0.1% to 2% by weight of a suspending agent capable of maintaining particulate matter in a more-or-less stable suspension are other embodiments herein. Suspending agents such as fumed colloidal silica or oleophilic Bentonite clays can be employed herein in the manner well-known to those skilled in the art to help stabilize such aerosol antiperspirant compositions containing the antiperspirant compounds of formula (I).

From the foregoing, it can be seen that antiperspirant compositions comprising one or more of the tetrakis-(trialkylsiloxy)titanium or tetrakis-(trialkylsiloxy)zirconium compounds of formula (I) in combination with all manner of compatible, pharmaceutically acceptable emollients, propellants, solvents and suspending agents, and mixtures thereof, can be prepared. The titanium and zirconium compounds of formula (I) can therefore be employed in antiperspirant formulations such as sprays, sticks, roll-ons, aerosols and the like. All manner of additives commonly found in cosmetic formulations can be employed in the preparation of said compositions to provide more cosmetically acceptable products.

The following examples are intended only to illustrate the compositions and processes of the invention but are not intended to be limiting thereof. The siloxy-titanates used in the examples are prepared in the manner of Bradley and Thomas, above. The siloxy-zirconates are prepared in the manner of Schlinger, et al., *Angew. Chem. Internat. Ed.*, 6, (1967) No. 8.

EXAMPLE I

Antiperspirant Powder

| Percent By weight | Ingredient |
|---|---|
| 15 | Tetrakis-(triethylsiloxy)titanate |
| 85 | Talc (powder; having an average particle size below about 37 microns) |

Application of the above composition to the human skin in amounts of about 1.0 milligram/mm$^2$ gives good antiperspirant results.

In the above composition, the tetrakis-(triethyl-siloxy)titanate is replaced by tetrakis-(trimethylsiloxy)-titanate, tetrakis-(triethylsiloxy)zirconate, tetrakis-(tri-tetradecylsiloxy)titanate, tetrakis-(tricyclohexyl-siloxy)titanate, tetrakis-(tricyclopentylsiloxy)zirconate and tetrakis-(tricyclodecylsiloxy)titanate, respectively and equivalent results are secured.

An effective dry powder antiperspirant is similarly prepared by admixing about 1% by weight of tetrakis-(trimethylsiloxy)titanate with commercial talc.

EXAMPLE II

"Dry" Aerosol Solution Antiperspirant

| Percent By weight | Ingredient |
|---|---|
| 10 | Tetrakis-(triethylsiloxy)zirconate |
| 0.1 | Hexachlorophene |
| 0.5 | Perfume |
| 3 | Lanolin (emollient) |
| Balance | Propellant* |

*Dichlorodifluoromethane and trifluoroethane, 80:20 weight mixture.

Application of about 0.1 g/cm$^2$ of the above composition to the skin gives good antiperspirant results.

In the above composition the tetrakis-(triethylsiloxy)-zirconate is replaced by an equivalent amount of tetrakis-(tripropylsiloxy)titanate, tetrakis-(tri-tetradecylsiloxy)titanate, respectively, and equivalent antiperspirant compositions are secured.

EXAMPLE III

Aerosol Solution Antiperspirant

| Percent By weight | Ingredient |
|---|---|
| 20 | Tetrakis-(triethylsiloxy)titanate |
| 20 | Ethyl alcohol - isopropyl alcohol (2:1 volume mixture) |
| 0.1 | Hexachlorophene |
| 0.7 | Perfume |
| Balance | Propellant* |

*Dichlorodifluoromethane and trifluoroethane, 60:40 weight mixture.

Application of about 1 g/24 cm$^2$ of the above composition to the skin gives good antiperspirant results.

EXAMPLE IV

Antiperspirant Stick

| Percent By weight | Ingredient |
|---|---|
| 1 | Tetrakis-(triethylsiloxy)zirconate |
| 95 | Polyoxyethylene gel |
| 0.2 | Perfume |
| Balance | Lanolin |

Application of about 25 g/24 cm$^2$ of the above composition to the skin gives good antiperspirant results.

EXAMPLE V

Roll-on Antiperspirant

| Percent By Weight | Ingredient |
|---|---|
| 5 | 1:1 (wt.) mixture of tetrakis-(triethylsiloxy)titanate and tetrakis-(triethylsiloxy)zirconate |
| 50 | Ethyl alcohol |
| 20 | Lanolin |
| 20 | Isopropyl myristate |
| 0.1 | Hexachlorophene |
| 0.5 | Perfume |
| Balance | Isopropyl alcohol |

Application of about 008 g/cm² of the above composition to the skin gives good antiperspirant results.

In the following test, the overall antiperspirant efficacy of representative tetrakis-(trialkylsiloxy)titanates and tetrakis-(trialkylsiloxy)zirconates was measured using aluminum chlorhydrate, a commercial antiperspiration ingredient, as the standard. In the test procedure, ca. 1.3 g. of a 10% (wt.) diethyl ether solution of tetrakis-(triethylsiloxy)titanate was absorbed on a cotton swab and applied to one axilla of volunteer subjects. In like fashion, a 10% (wt.) solution of tetrakis-(triethylsiloxy)zirconate was applied to one axilla of test subjects. A freshly prepared 10% (wt.) aqueous solution of aluminum chlorhydrate was applied in similar fashion to the other axilla of each test subject. Perspiration flow was induced in the test subjects by an exercise-rest regimen in a temperature chamber at 110°F and 47% relative humidity. Perspiration was collected using weighted cotton pads and the perspiration flow from each axilla was established gravimetrically. On the average, the tetrakis-triethylsiloxy)titanate caused a 48% reduction in perspiration flow in test subjects as compared to a 27% reduction for aluminum chlorhydrate in the same test. The tetrakis-(triethylsiloxy)zirconate caused a 45% reduction in perspiration flow as compared with a 38% reduction in perspiration flow caused by aluminum chlorhydrate in the same test. The foregoing data illustrate the superior antiperspirant effectiveness of representative tetrakis(trialkylsiloxy)titanates and tetrakis-(trialkylsiloxy)-zirconates over the most widely used antiperspiration ingredient.

It is to be understood that the siloxy-titanates and siloxy-zirconates herein can be used in conjunction with any of the commercially used antiperspiration agents (e.g., aluminum chlorhydrate, aluminum chloralcoholates, zirconium oxychloride and the like) to provide antiperspirant compositions having "mixed" antiperspiration ingredients.

What is claimed is:

1. A method for inhibiting perspiration comprising applying to human skin an effective amount of a tetrakis(trialkylsiloxy) compound of the formula $$M(OSiR_3)_4$$

wherein M is selected from the group consisting of titanium and zirconium and wherein each substituent R is alkyl, cycloalkyl or branched chain alkyl of from about $C_1$ to $C_{14}$.

2. A method according to claim 1 wherein each substituent R in the tetrakis-(trialkylsiloxy) compound is $C_1$ to $C_3$ alkyl.

3. A method according to claim 2 wherein the tetrakis-(trialkylsiloxy) compound is a member selected from the group consisting of tetrakis-(triethylsiloxy)-titanate and tetrakis-(triethylsiloxy)zirconate.

* * * * *